United States Patent [19]

Corrie et al.

[11] Patent Number: 5,434,272
[45] Date of Patent: Jul. 18, 1995

[54] PHOTO-LABILE COMPOUNDS, THEIR SYNTHESIS AND USE AS FLUOROPHORES

[75] Inventors: John E. T. Corrie; David R. Trentham, both of London, United Kingdom

[73] Assignee: Medical Research Council, England

[21] Appl. No.: 50,390

[22] PCT Filed: Nov. 6, 1991

[86] PCT No.: PCT/GB91/01941
§ 371 Date: May 6, 1993
§ 102(e) Date: May 6, 1993

[87] PCT Pub. No.: WO92/08720
PCT Pub. Date: May 29, 1992

[30] Foreign Application Priority Data

Nov. 7, 1990 [GB] United Kingdom ............... 9024176

[51] Int. Cl.⁶ .................................... C07D 311/82
[52] U.S. Cl. ................................ 548/525; 549/223
[58] Field of Search .................... 549/223; 548/525

[56] References Cited

FOREIGN PATENT DOCUMENTS

| 0233403 | 8/1987 | European Pat. Off. |
| 2500165 | 8/1982 | France |
| 9003401 | 4/1990 | WIPO |

OTHER PUBLICATIONS

J. F. Burd et al., Analytical Biochemistry, 77(1), 1977, pp. 56–57.
G. A. Kraft et al., Journal of the American Chemical Society, 110(1), 1988, pp. 301–303.

*Primary Examiner*—C. Warren Ivy
*Assistant Examiner*—A. A. Owens
*Attorney, Agent, or Firm*—Wenderoth, Lind & Ponack

[57] ABSTRACT

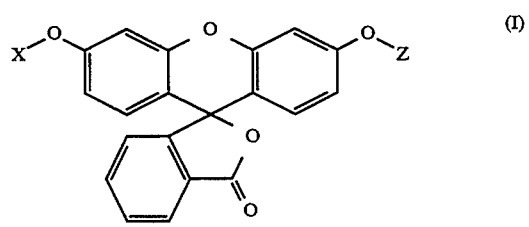

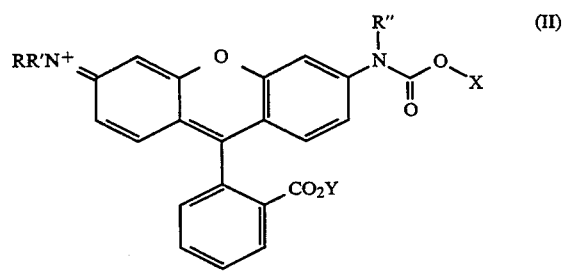

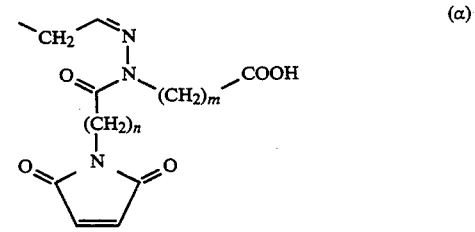

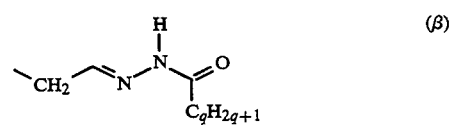

Compounds of formulae (I), (II) wherein X is an optionally substituted benzyl group which carries an $NO_2$ group in the ortho-position, Z is a group of formula $\alpha$ or $\beta$, R, R' and Y are each optionally substituted groups, R" is hydrogen or alkyl, m and n are each integers of from 1 to 6, and q is an integer of from 1 to 20, and salts thereof. These protected or caged organic compounds, based on the dyes fluorescein (I) and rhodamine (II), can be introduced into biological systems and there released by means of light radiation. They are suitable, for example, for use in the labelling of proteins or lipophilic structures. Processes for the preparation of the compounds are also described.

3 Claims, 1 Drawing Sheet

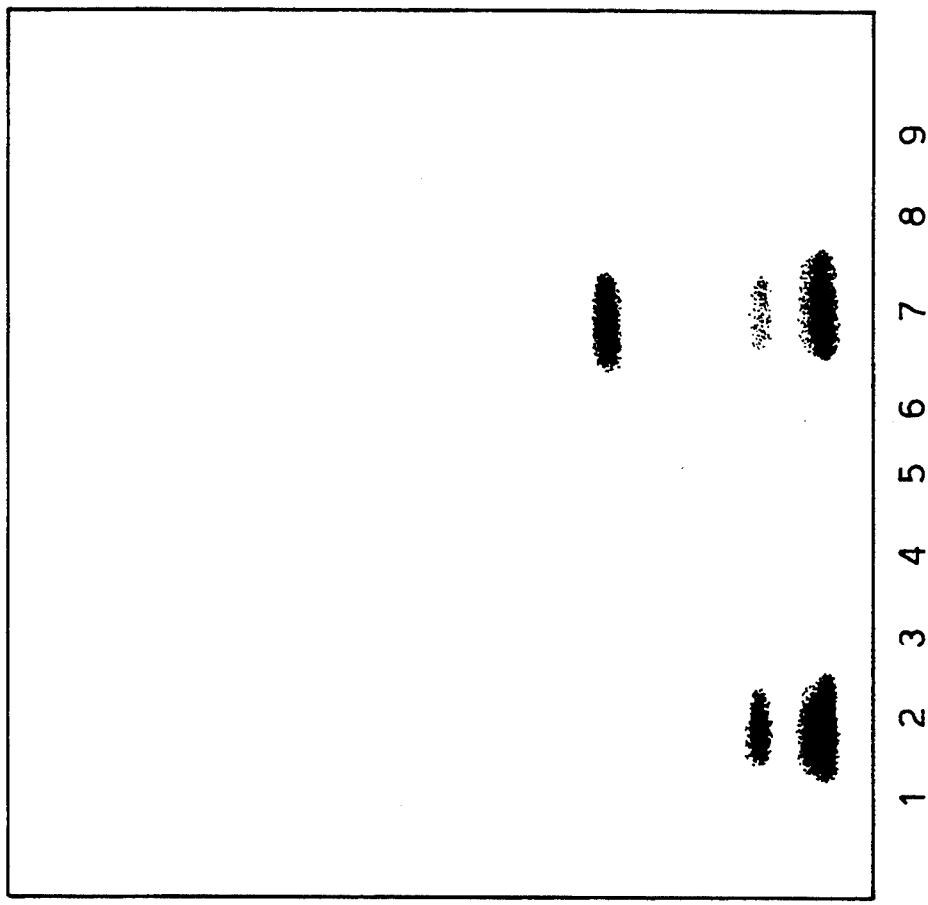
Fig. 1. SDS-POLYACRYLAMIDE GEL ELECTROPHORETOGRAM OF MYOSIN LIGHTCHAIN-1 (LC-1) LABELLED WITH CAGED FLUORESCEIN-MALEIMIDE (9)

PHOTO-LABILE COMPOUNDS, THEIR SYNTHESIS AND USE AS FLUOROPHORES

This application is a 371 of PCT/GB91/01941 filed Nov. 6, 1991.

This invention relates to novel protected or "caged" organic compounds, based on the dyes fluorescein and rhodamine, which can be introduced into biological systems and there released by means of light radiation. These photo-labile compounds, or photoactivatable fluorophores, are suitable for use in labelling proteins. Processes for the preparation of the compounds are also described.

The study of the structure and dynamics of cellular and other biological systems by the attachment of fluorescent labels to molecular species is a well known and widely used approach. A technique which has been reported in recent years is fluorescence photoactivation and dissipation (FPD). This technique was first described by Ware et al. in Applications of Fluorescence in the Biomedical Sciences, 141–157, 1986, Edited by Taylor et al., Liss, New York. The basic feature of an FPD measurement is the attachment of a molecular label that is initially non-fluorescent but which will become fluorescent when exposed to a short pulse of light of the appropriate wavelength. Such molecules are called photoactivatable fluorophores (PAF).

Krafft et al., J. Am. Chem. Soc., 1988, 110, 301–303, describe photoactivatable fluorophore compounds based on difunctionalised fluoresceins. The development of such compounds was prompted by the fact that fluorescein can exist as either of two tautomeric forms: a fluorescent, xanthen-3-one form or a non-fluorescent, lactone form. The compounds are held in the non-fluorescent lactone tautomer through dialkylation of the two phenolic oxygens, with one of the ether groups being susceptible to a photo-cleavage reaction that triggers the opening of the lactone structure to produce the fluorescent xanthen-3-one tautomer.

The invention shows that the fluorescence of rhodamine, on the other hand, is quenched by introducing electron-withdrawing groups onto the amine groups, thereby reducing electron delocalisation throughout the aromatic system.

Mitchison, The Journal of Cell Biology, 109, 1989, 637–652, describes the use of a derivative of carboxyfluorescein, the synthesis of which is based on the work of Krafft et al. (op. cit.). The compound is non-fluorescent, but can be converted to a fluorescent form by exposure to light of 365 nm wavelength. This photoactivatable fluorescent probe was covalently attached to a globular protein, tubulin, and micro-injected into mitotic cells in tissue culture (where it incorporated into functional spindles).

Notwithstanding the above, the compounds described by Krafft et al. and by Mitchison suffer from certain disadvantages which include difficulties in synthesis. For example, the methods for their preparation do not permit clean substitution of single photo-sensitive groups on one of the two phenolic oxygens and this results in the need for extensive chromatographic purification. This is an important point because the presence of as little as 1% of free fluorophore in the photoactivatable compound is sufficient to seriously restrict its effective use in biological research. The compounds described by Krafft et al. and by Mitchison also suffer from a relative lack of water solubility, which is an important property when considering the labelling of biological molecules. Furthermore, the compounds of Krafft et al. and of Mitchison are all based on fluorescein. It will be appreciated that a range of probes with differing optical properties would be desirable.

There is therefore a need for further compounds suitable for use as photoactivatable fluorophores and which have more controlled syntheses incorporating crystalline intermediates and also having improved properties, such as water solubility and the ability to bind at specific sites on proteins, or a lipophilic nature and the ability to bind to lipid structures.

The present invention seeks to provide such compounds and processes for their preparation.

According to the present invention there are provided compounds of the following formulae (I) and (II):

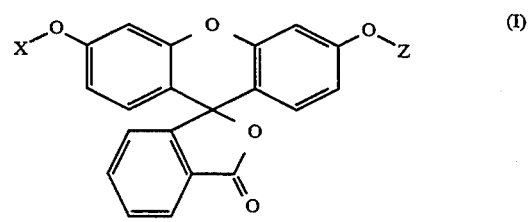

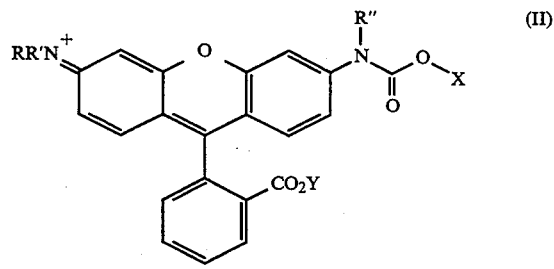

wherein X is an optionally substituted benzyl group which carries a $NO_2$ group in the ortho-position, Z is a group of the formula:

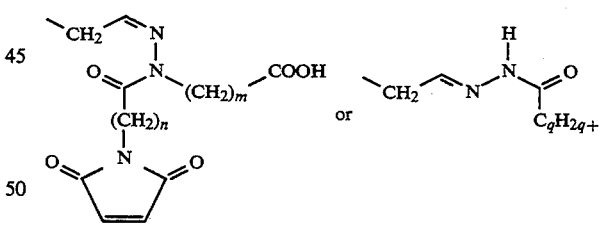

R, R' and Y are each optionally substituted groups,
R" is hydrogen or alkyl, and
m and n are each integers of from 1 to 6,
q is an integer of from 1 to 20, and salts thereof.

Groups R, R' and Y are each optionally substituted and this permits the introduction of water-solubilising and protein-reactive functions into the compounds. The person skilled in the art will readily appreciate the variety of substituent groups available and the criteria for selecting those which will impart the desired properties or characteristics to the final compound. For example, groups R, R' and Y may be lower ($C_1$-$C_6$) alkyl chains substituted individually or severally with ionisable functions such as carboxylate or sulphonate, and/or with functions specific for protein labelling such as maleimides, haloacetates or reactive esters. The multifunctional side chain shown in structure (I) represents one such example. R" is hydrogen or alkyl, most typically lower ($C_1$-$C_6$) alkyl.

The compounds (I) and (II) are photocleavable and are useful as photoactivatable fluorophores. It will be appreciated that the fluorophore comprises fluorescein in compound (I) and rhodamine in compound (II). It will be further appreciated that, depending upon the identity of the sidechain of substituent Z, the compounds (I) will exhibit either good water solubility or strong lipophilic properties, and this will obviously influence their areas of use.

A particularly preferred photoactivatable compound of this invention has the following formula:

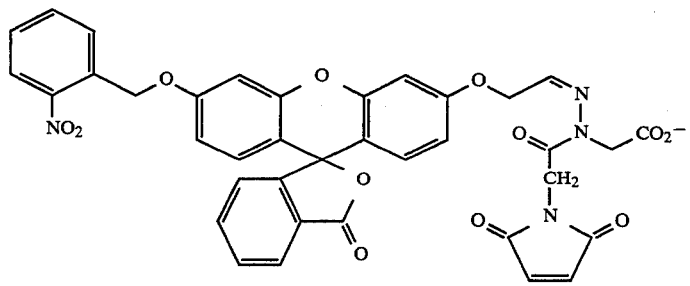

According to the present invention there is further provided a method for preparing the compounds (I) and which comprises the following sequence of reactions:

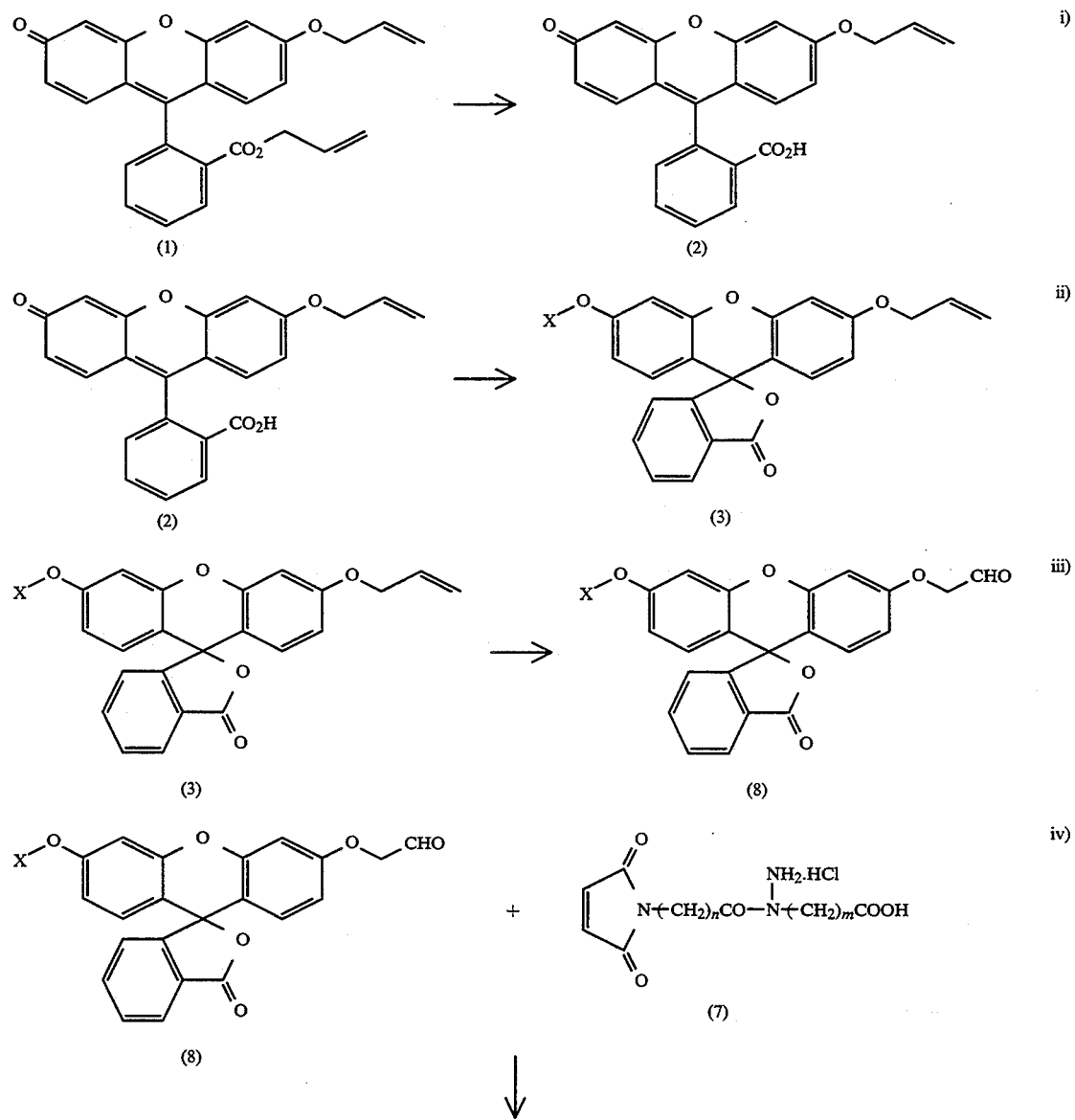

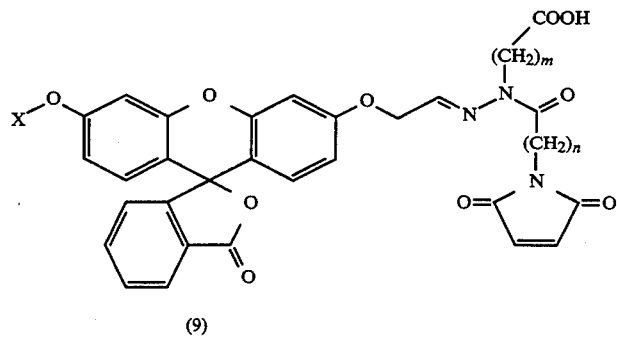
(9)
In an alternative approach, suitable where the fluorophore constituent is rhodamine, the invention provides a method for preparing the compounds (III) and which comprises the following sequence of reactions:
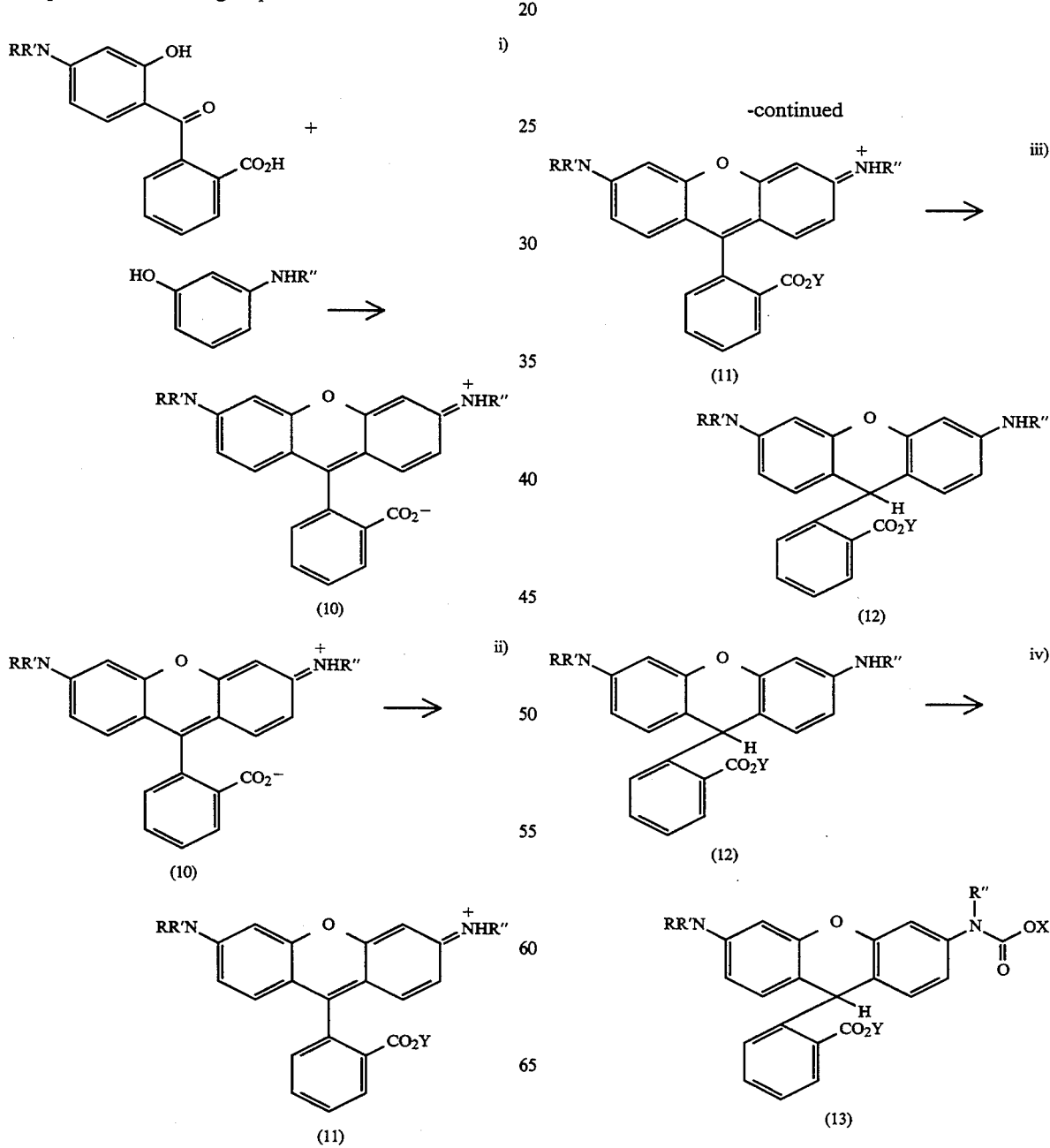

-continued

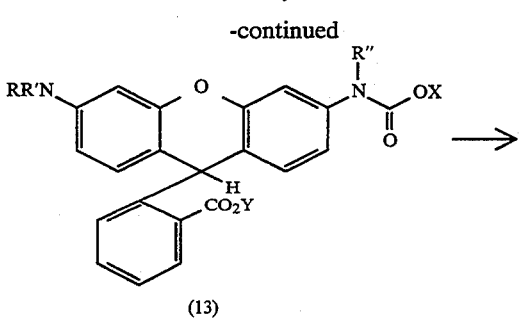

(13)

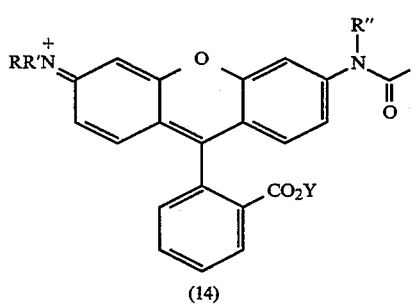

(14)

The intermediate compound of the following formula, referred to in the above reaction sequence, is a novel compound and is a further aspect of this invention:

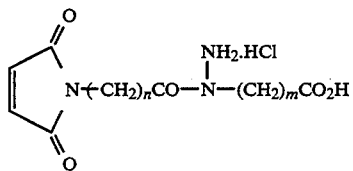

(7)

A still further aspect of the invention is a method for preparing the compound (7) and which comprises the steps shown in the following Reaction Sequence 1.

the fluorescent signal is then followed. Procedures for achieving the introduction, such as micro-injection techniques, are well known and need not be described here in detail.

The conditions required for photolysis of the compounds are the same as with conventional photocleavable ortho-nitrobenzyl compounds. Light having a wavelength of from 300 to 350 nm is suitable for this purpose such as may be generated by a xenonarc flash lamp or a 347 nm frequency doubled ruby laser. Longer exposure from a filtered (300 to 350 nm) mercury or xenon-arc lamp source is perfectly adequate when high time resolution is not required. The photoactivatable fluorophore may be illuminated through a microscope in order to achieve appropriate spatial resolution within the biological system.

The invention thus provides a range of new compounds suitable for use as photoactivatable fluorophores and which are synthesised through the use of a novel intermediate compound (7). The compounds exhibit good water solubility, typically have a simple and specific reaction with the thiol group of the cysteine side chain in protein molecules and possess spectroscopic properties desirable for their intended use. Certain of the compounds of formula (I) exhibit highly lipophilic properties and are thus suited for use in the labelling of lipid structures. The method by which they are formed is relatively clean, efficient and produces good yields.

The compounds (I) and (II) of the invention are designed for use in biological studies and are, for example, ideally suited for use in the aforementioned fluorescence photoactivation and dissipation (FPD) technique. As will be appreciated, once a label has been introduced into a biological system, it is possible to follow the movement and function of the labelled molecules, typically proteins, and their interaction with other components of the cell system. It has previously been shown that proteins labelled with fluorophores will be incorporated into the filamentous proteins characteristic of the Reaction Sequence 1

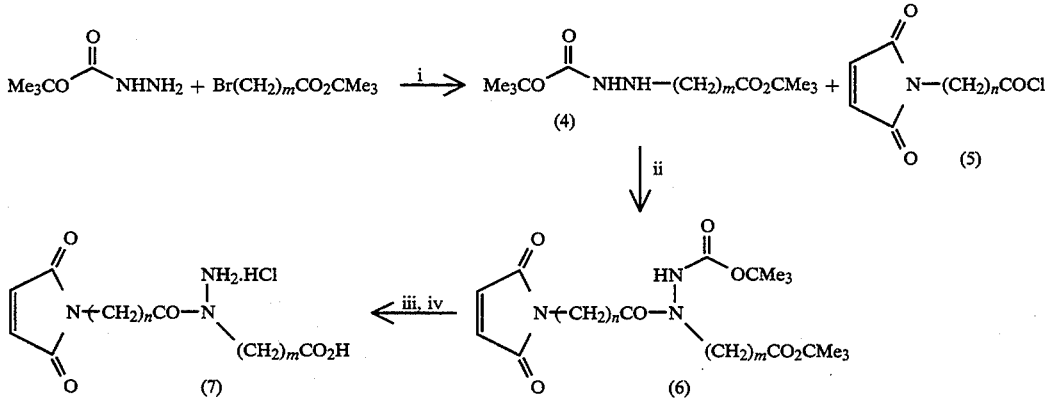

Reagents: i) Et$_3$N/benzene/heat; ii) Et$_3$N/Et$_2$O/0°; iii) CF$_3$CO$_2$H; iv) HCl/dioxan The compounds (I) and (II) of this invention are photocleavable and find use as photoactivatable fluorophores for the labelling of, for instance, proteins and lipid structures. For example, they can be used to label proteins at the site of a cysteine side chain. Such a labelled protein is introduced into a biological system, and is there photoactivated so as to form the fluorescent compound in situ in the biological system. The fate of internal cell structure and this can provide useful information about cell structure and the cell cycle (e.g. mitosis). With the compounds (I) and (II) of the invention, there is the additional advantage that the fluorescent label can be released at a localised point in the cell and the fate of the labelled protein can then be followed as a function of time. This allows the investigation of spatial movement and diffusion rates in a cellular system.

The compounds and method of this invention will now be further illustrated by the following Examples. Examples 1 and 3 relate to the preparation of a caged fluorescein compound of the invention; Example 2 refers to the synthesis of the novel intermediate compound used in this preparation. Example 4 demonstrates the labelling of a protein thiol with the caged fluorescein compound. Example 5, which is included to illustrate the preparation of compounds based on rhodamine, refers to a model of the chemistry in which the acyl group on one of the amines is acetyl (i.e. it blocks the fluorescence by electron withdrawal, but is not photocleavable). Example 6 relates to the synthesis of a caged fluorescein compound of the invention and which has a highly lipophilic nature.

EXAMPLE 1

Fluiorescein monoallyl ether (2) was prepared by hydrolysis of fluorescein allyl ether ester (1) using a modification of the method of Hurd & Schmerling[1]. Thus the ether ester (1; 2 g) dissolved in hot acetone (100 ml) was treated with 1.25M NaOH (60 ml) and the solution was heated under reflux for 12 minutes, then poured into water (200 ml). The solution was acidified with concentrated HCl and the precipitated solid was filtered, washed with water and recrystallised from ethanol to afford the monoether (2) as yellow crystals (0.83 g, 46%), m.p. 206°–7° C. (lit.[1] 205° C.).

3'-O-(2-Nitrobenzyl) -6'-O-allylfluorescein [(3) where X=2-nitrobenzyl]. The preparation of this compound was based on the method of Krafft, Sutton & Cummings.[2] Thus a suspension of the allyl ether (2; 0.80 g) in dry benzene (14.5 ml) and dry tetrahydrofuran (4.5 ml) was treated with 2-nitrobenzyl bromide (0.746 g) and silver (I) oxide (1.02 g) and stirred under reflux in the dark for 16 hours. The mixture was cooled, filtered and the precipitate washed with ethyl acetate. The combined filtrates were evaporated and the residue purified by flash chromatography (Merck*9385 silica gel) using $CH_2Cl_2$-petroleum ether (75:25) as the eluting solvent. Fractions containing the product were combined, the solvent was evaporated and the residue was triturated with ether to afford the product (3) as a colourless solid (0.68 g; 62%), which crystallised from ethyl acetate-petroleum ether as plates, m.p. 171°–2° C. (Found: C, 71.1; H, 4.2; N, 2.7. $C_{30}H_{21}NO_7$ requires C, 71.0; H, 4.2; N, 2.8%).
*Registered trade mark

EXAMPLE 2 t-Butyl N'-(t-Butoxycarbonylmethyl)hydrazinecarboxylate [(4) where m,n=1]. The compound was prepared by modification of the method of Streicher and Reinshagen[3] for the corresponding ethyl ester. Thus a solution of t-butyl carbazate (5.28 g), t-butyl bromoacetate (7.80 g) and triethylamine (4.06 g) in dry benzene (40 ml) was heated under reflux for 16 hours, cooled and filtered. The filtrate was washed with saturated $NaHCO_3$ and brine, dried and evaporated. The residue was dissolved in ethanol (85 ml) which contained pyruvic acid (4.4 g) and 4M NaOAc (11.5 ml) was added. After standing for 1 hour at room temperature the mixture was diluted with ether, washed with saturated $NaHCO_3$ and brine, dried and evaporated. The residue was distilled to give the product (4) as a colourless viscous liquid (2.8 g; 28%) which crystallised on standing, m.p. 48°–9° C. (Found: C, 54.0; H, 9.3; N, 10.95. $C_{11}H_{22}N_2O_4$ requires C, 53.6; H, 9.0; N, 11.4%).

t-Butyl N'-(t-Butoxycarbonylmethyl)-N'-(2-(2,5-dihydro-2,5-dioxopyrrol-1-yl)acetyl)hydrazinecarboxylate [(6) where m,n=1]. A suspension of 2,5-dihydro-2,5-dioxopyrrol-1-ylacetic acid (821 mg) in thionyl chloride (15.9 ml) was heated under reflux for 0.5 hours and the excess thionyl chloride was removed under vacuum. The residue was evaporated twice with dry toluene to afford 2,5-dihydro-2,5-dioxopyrrol-1-ylacetyl chloride [(5) where m=1] as a colourless, readily hydrolysed liquid. (The compound has been prepared previously by a less convenient route[5]). The crude acid chloride was dissolved in dry ether (25 ml) and added dropwise to an ice-cold solution of the hydrazinecarboxylate [(4) where n=1, 1.30 g] and triethylamine (588 mg) in dry ether (25 ml). The mixture was stirred in an ice bath for 1 hour then diluted with ethyl acetate and washed with water, dilute HCl, saturated $NaHCO_3$ and brine, dried and evaporated. The residue was crystallised from ethyl acetate—petroleum ether to give the compound (6) as colourless plates (1.67 g; 82%) m.p. 157°–9° C. (Found: C, 53.1; H, 6.7; N, 10.8. $C_{17}H_{25}N_3O_7$ requires C, 53.25; H, 6.6; N, 11.0%).

N-Carboxymethyl-2(2,5-dihydro-2,5-dioxopyrrol-1-yl)acetyl hydrazide hydrochloride [(7) where m,n=1].

The compound (6; 400 mg) was dissolved in trifluoroacetic acid (1.5 ml) and kept at room temperature for 1 hour. The trifluoroacetic acid was evaporated under reduced pressure and the residue was redissolved in a 2M solution of anhydrous HCl in dioxan (4 ml). Colourless crystals began to separate after a few minutes and the solution was diluted with dry isopropyl ether (10 ml), filtered and the precipitate washed with isopropyl ether and dried to give the hydrochloride (7) which contained 0.5 equivalent dioxan of solvation (256 mg, 79%).

EXAMPLE 3

Caged fluorescein-maleimide [(9) where m,n=1, X=2-nitrobenzyl]. A solution of the 2-nitrobenzyl allyl fluorescein (3; 51 mg) in $CH_2Cl_2$ (10 ml) and MeOH (0.2 ml) was cooled to −50° C. and treated with a stream of ozonised oxygen until t.l.c. analysis (silica gel; ethyl acetate—petroleum ether 1:1) showed complete consumption of the starting material (ca. 30 minutes). The solution was purged with nitrogen, treated with dimethyl sulphide (0.10 ml) and allowed to warm to room temperature over 1 hour, then stirred for a further 1 hour, diluted with $CH_2Cl_2$, washed with water and brine, dried and evaporated. The residue was purified by flash chromatography (ethyl acetate—light petroleum 1:1) to afford the aldehyde [(8) where X=2-nitrobenzyl] as a pale gum (36 mg) which was characterised by $^1$H-NMR spectroscopy. This material was dissolved in dimethyl formamide (0.2 ml) and treated with a solution of the hydrazide hydrochloride [(7) where m,n=1; 26 mg] in EtOH (0.3 ml) and 2M NaOAc (0.06 ml). The solution was kept in the dark for 2 hours at room temperature then diluted with ethyl acetate and washed with 1M citric acid and brine, dried and evaporated. The residue was purified by flash chromatography (ethyl acetate-methanol-acetic acid 95:5:0.5) to give the product (9) as a pale gum (24 mg), which was characterised by $^1$H NMR. The material was stored in the dark at 4° C. as a dilute solution in EtOAc.

After addition of 2-mercapto ethylsulphonate to the maleimide group, the quantum yield for photolysis was 0.65 (irradiation 300–350 nm) and the rate of release of the fluorophore was 7s$^{-1}$, both measurements being at pH 7.0 and 22° C.

EXAMPLE 4

Labelling a protein thiol with caged fluorescein-maleimide (9). Myosin light chain-1 (LC-1) was dissolved at 1 mg/ml in a solution of 50 mM Tris-HCl/2 mM EDTA/2 mM dithiothreitol at pH 7.5 and kept for 15 minutes then dialysed for 2 hours against 10 mM PIPES/2 mM EDTA/2 mM ascorbate, pH 6.5. One aliquot, A, (1 ml) was treated with an aliquot (0.10 ml) of a solution containing 400 mM sodium phosphate/2 mM ascorbate/8 mM N-ethylmaleimide, pH 7.5 and incubated for 20 minutes at room temperature. A further aliquot, B, (1 ml) was treated with aliquot (0.10 ml) of a solution containing 400 mM sodium phosphate/2 mM ascorbate, pH 7.5 and incubates A and B were then immediately treated with aliquots (0.10 ml) of a solution of 8 mM caged fluorescein-maleimide [(9) where X=2-nitrobenzyl, m,n=1] in dimethyl formamide. Each solution was kept for 30 minutes in the dark at room temperature, then excess reagent was quenched by addition of aliquots (50 μl) of 40 mM mercaptoethanol in 10 mM Tris-HCl, pH 7.5. Each incubate was dialysed for 2 hours in the dark against 10 mM Tris-HCl, pH 7.5 and subjected to gel filtration on Sephadex* G50 (1 g dry weight) in the same buffer. Fractions containing the protein were pooled and aliquots were irradiated (300–350 nm waveband) until maximum release of fluorescence was observed (ca. 30 seconds with a 100 W lamp). The irradiated solutions were analysed by SDS-polyacrylamide gel electrophoresis (approx. 2 μg labelled protein per track) and the gel was photographed under ultraviolet illumination to detect fluorescent bands. Subsequent staining with Coomassie Blue identified the position of the myosin light chain-1. FIG. 1 shows the experimental result and reveals the presence of significant quantities of free dye, i.e. not covalently bound to the protein and dissociating during the electrophoresis run. Further processing of the caged fluorescein-labelled protein by f.p.l.c. on a Mono Q column (Pharmacia) gave fractions which when analysed as above were entirely free of non-covalently bound dye.

* Registered trade mark

EXAMPLE 5 (see Reaction Sequence 2)

3-Amino-6-diethylamino-9-(2-methoxycarbonylphenyl) xanthylium chloride (11). The synthesis of unsymmetrical rhodamines followed long established methods, e.g. Ref. 6 and references therein. A mixture of 3-aminophenol (0.57 g), 2-(2-hydroxy-4-diethylaminobenzoyl)benzoic acid (1.5 g) and concentrated sulphuric acid (9 ml) was heated at 105° C. for 4 h, cooled and poured slowly into an ice cold solution of KOH (18.9 g) in water (50 ml). The solution was adjusted to pH 2–3 with dilute KOH and the precipitate was filtered and dried in vacuo. The dried solid was dissolved in MeOH, filtered from inorganic salts and evaporated to leave the crude rhodamine (10) as a dark solid (1.92 g; 107%). This material was dissolved in MeOH (20 ml) and hydrogen chloride was bubbled into the solution for 20 min, then for a further 3 h while the solution was heated at 60° C. The solution was concentrated to approx. 7 ml, diluted with water and extracted with CHCl$_3$. The organic extract was dried and evaporated to give the crude ester (11) as a dark solid (2.2 g; 105%), $\lambda_{max}$ 531.5 nm ($\epsilon$66,300).

3-Amino-6-diethylamino-9-(2-methoxycarbonylphenyl)xanthene (15).

Preparation of this compound was based on the method of Sensui, Gonda and Obara[7]. Thus a portion (0.50 g) of the crude ester (11) was dissolved in MeOH (25 ml) and sodium borohydride was added in portions over 2 h, until the initial dark red colour was discharged (total NaBH$_4$ approx. 0.2 g). The solution was stirred for a further 1 h at room temperature, concentrated under reduced pressure to a small volume, diluted with water and extracted with chloroform. The extract was dried and evaporated to leave a pale gum (355 mg) which showed the presence of the xanthene (15) on t.l.c. (silica gel; benzene) as a colourless spot, $R_f$ approx. 0.5, which rapidly turned red on exposure to light and air.

3-Acetamino-6-diethylamino-9-(2-methoxycarbonylphenyl)xanthene (16). The aminoxanthene (15; 175 mg) was dissolved in CHCl$_3$ and treated with triethylamine (450 mg) and acetyl chloride (175 mg). The solution was stirred at room temperature for 1 h, evaporated to dryness and the major component isolated by flash chromatography, initially with ethyl acetate—light petroleum (3:5) which eluted non-polar impurities, followed by chloroform which gave the acetylated product (16) as a pale pink foam (102 mg; 52%) after removal of the solvent. Particular features of the $^1$H NMR spectrum which confirmed the structure of the product were signals at δ 6.11 (s, 1H, H-9) and 2.09 (s, 3H, acetyl).

Analogous compounds were obtained when 2-nitrobenzyl chloroformate or 1-(2-nitrophenyl)ethyl chloroformate were used in place of acetyl chloride.

3-Acetimino-6-diethylamino-9-dehydro-9-(2-methoxycarbonylphenyl)xanthene (17). The preparation of this compound by tetrachlorobenzoquinone oxidation was based on the method of Sensui, Gonda and Obara.[7] The acetamino compound (16; 100 mg) was dissolved in glacial acetic acid (0.5 ml) and tetrachlorobenzoquinone (100 mg; 1.8 equivalents) was added. The colour of the solution immediately turned to deep red. Chloroform (3 ml) was added and the solution was stirred for 1 h at room temperature, then further diluted with chloroform and washed with saturated NaHCO$_3$, dried and evaporated. The residue was purified by flash chromatography in CHC$_3$-EtOH 20:1, which eluted non-polar components, followed by CHCl$_3$-EtOH 10:1 and 4:1 to elute the product (17) which was obtained as a deep red solid (78 mg), $\lambda_{max}$ 499,533 nm ($\epsilon$ 35,200 and 38,300). In the $^1$H NMR spectrum, the downfield shift of the acetyl signal (δ 2.40) as compared to its position in the reduced precursor (16) was consistent with the proposed structure.

Reaction Sequence 2

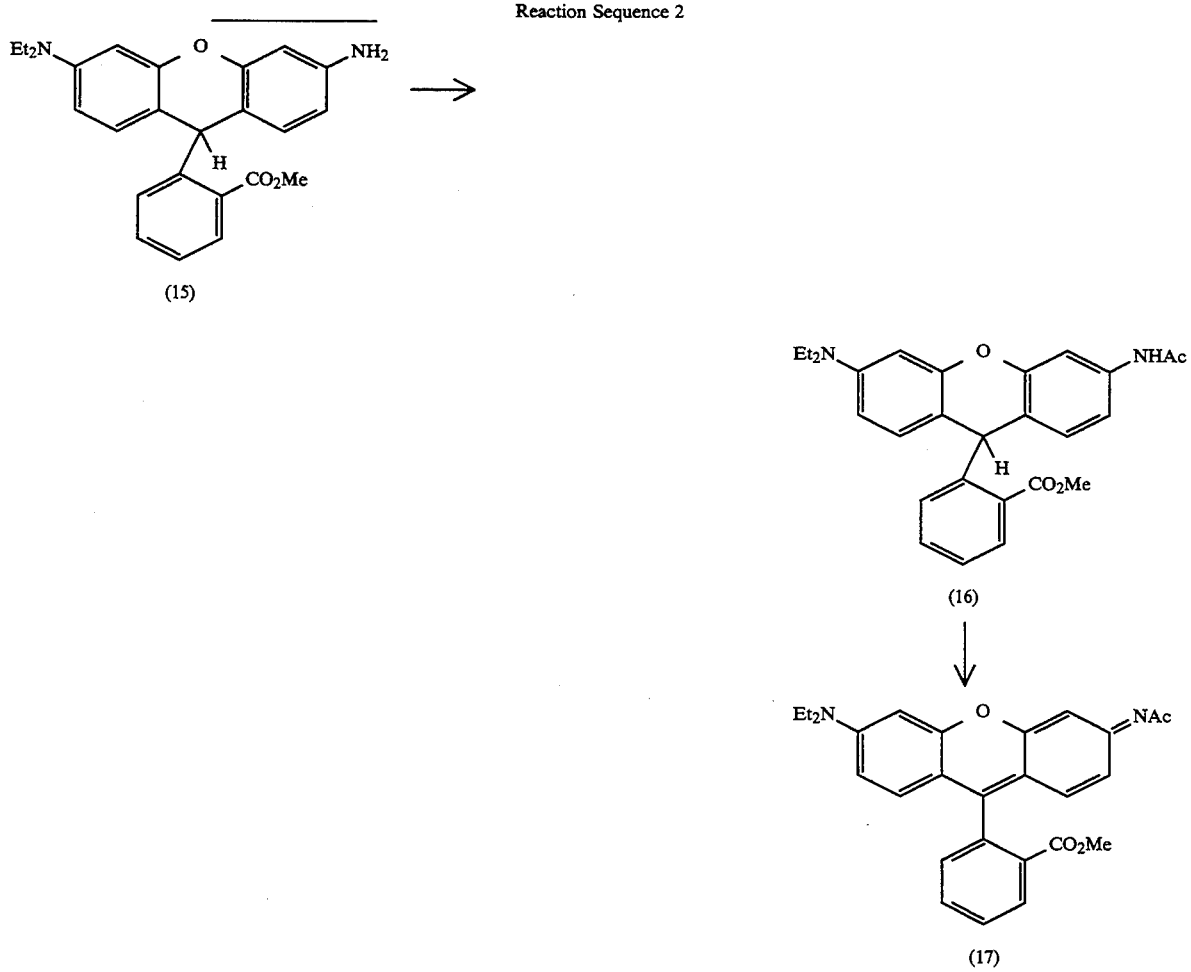

The relative fluorescence intensities of the compounds (11), [R,R',R"=Et, Y=H] and (17) were approximately 57:1.

EXAMPLE 6

3'-O-(2-Nitrobenzyl)-6'-O-(3,4-diaza-5-oxoeicos-2-en-1-yl)fluorescein (18).

The aldehyde (8) was prepared by ozonolysis of 2-nitrobenzyl allyl fluorescein (3; 51 mg) as described in Example 3, and mixed with a solution of palmitic hydrazide (40 mg, prepared as described by Curtius and Dellschaft[8]) in ethanol (0.9 ml) and tetrahydrofuran (0.3 ml). The solution was heated under reflux for 1 h and the solvent evaporated under reduced pressure. The residue was purified by flash chromatography (ethyl acetate—$CH_2Cl_2$ 15:85) to afford the lipophilic hydrazone (18) as a colourless glass (46 mg) which was characterised by $^1$H-NMR spectroscopy.

The product has the following formula:

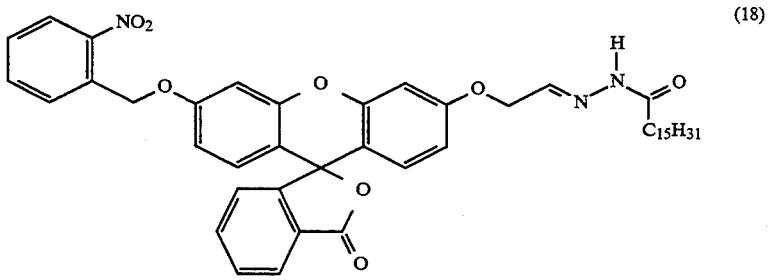

This is a caged fluorescein compound with a highly lipophilic nature and is suitable for use in the labelling of lipid bilayers or other lipid structures.

1. C. D. Hurd and L. Schmerling, J. Am. Chem. Soc., 1937, 59, 113.
2. G. A. Krafft, W. R. Sutton and R. T. Cummings, J. Am. Chem. Soc., 1988, 110, 301.
3. W. Streicher and H. Reinshagen, Chem. Ber., 1975, 108, 813.
4. D. H. Rich, P. D. Gesellchen, A. Tong, A. Chueng and C. K. Buchner, J. Med. Chem., 1975, 18, 1004.
5. L. Paul, A. Dittmar and C. Rusch, Chem. Ber., 1967, 100, 2757.

6. C. D. Ritchie, J. A. Wenniger and J. H. Jones, J. Ass. Off. Agric. Chem., 1959, 42, 720.
7. H. Sensui, M. Gonda and T. Obara, Eur. Patent Appl. 184 114.
8. T. Curtius and F. H. Dellschaft, J. Prakt. Chem., 1901, 64, 419.

BRIEF DESCRIPTION OF DRAWING

Lanes 2 and 7 contain equal masses of protein, but the LC-1 in lane 2 (incubate A in Example 4) had been pretreated with N-ethylmaleimide prior to treatment with the caged fluorescein-maleimide. The LC-1 in lane 7 is derived from incubate B and shows specific incorporation of the caged fluorescein. As described in the labelled protein preparations were irradiated prior to electrophoresis to release the fluorescence of the caged species, and the gel was photographed under ultraviolet irradiation to visualise fluorescent species.

We claim:

1. A compound having the following formula:

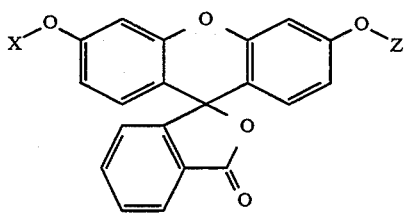

(I)

wherein X is an optionally substituted benzyl group which carries a $NO_2$ group in the ortho-position, Z is a group of the formula:

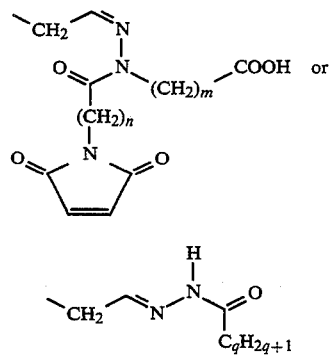

$m$ and $n$ are each integers of from 1 to 6, and $q$ is an integer of from 1 to 20, and salts thereof.

2. A compound as claimed in claim 1 of the formula:

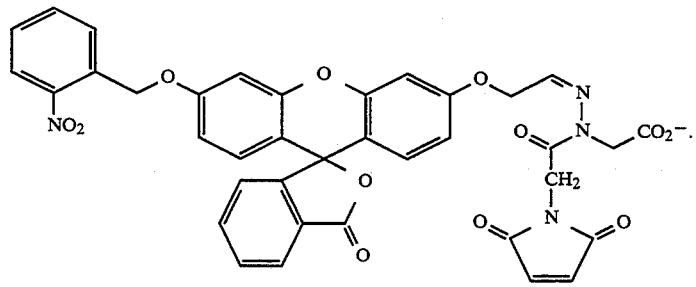

3. A method for preparing a compound (I) as claimed in claim 1, which comprises the following sequence of reactions:

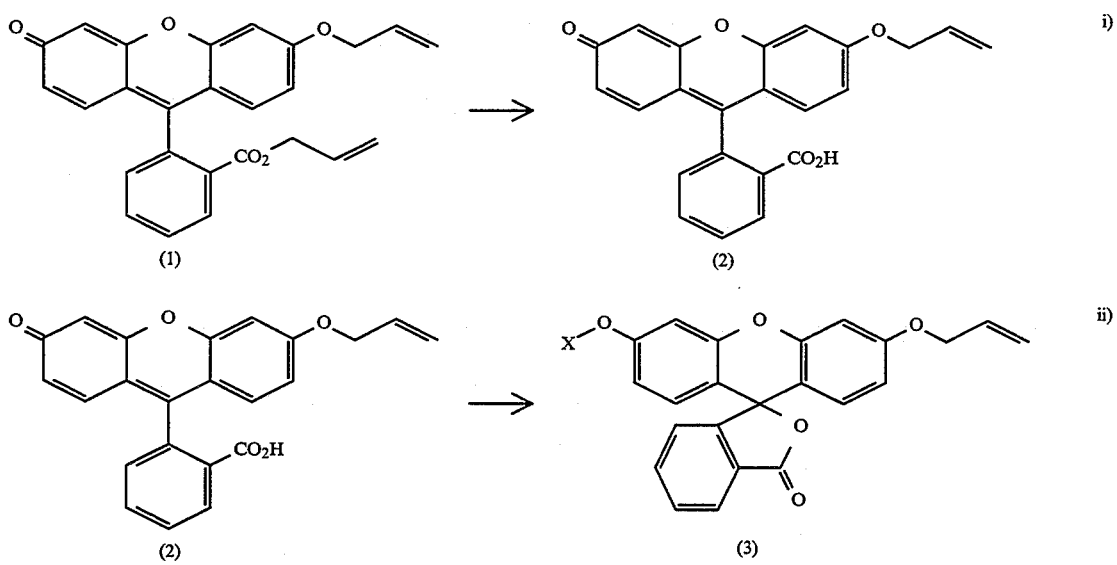

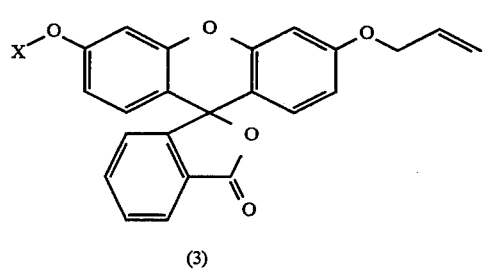
(3)
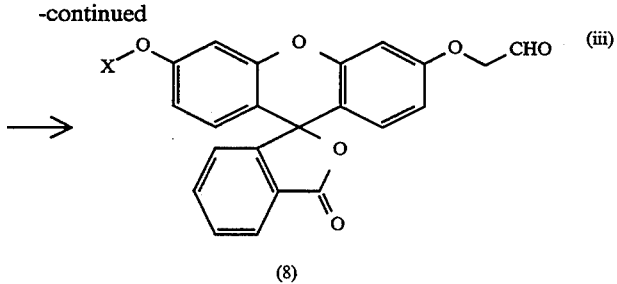
(8)
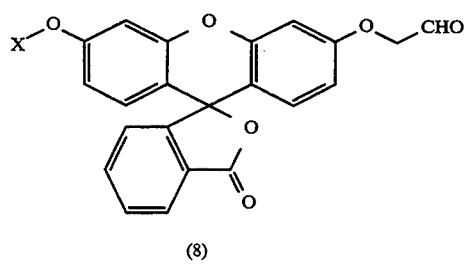
(8)
+
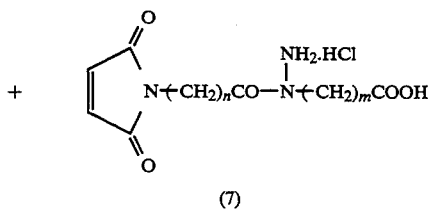
(7)
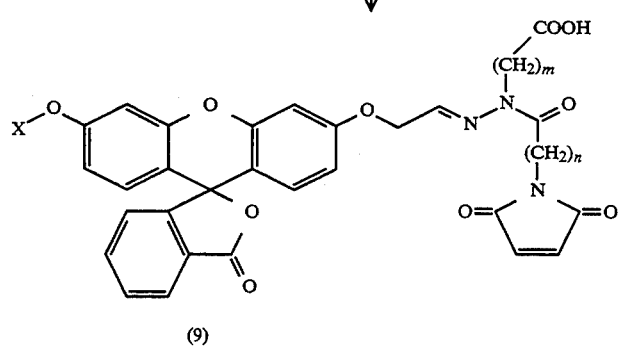
(9)
wherein X is an optionally substituted benzyl group which carries a NO₂ group in the ortho-position, and m and n are each integers of from 1 to 6, and salts thereof.
* * * * *